United States Patent [19]

King et al.

[11] Patent Number: 4,870,216

[45] Date of Patent: Sep. 26, 1989

[54] PHENOL ALKYLATION PROCESS

[75] Inventors: Jeffrey F. King; Charles W. Matthews, both of Orangeburg, S.C.; Eric S. Batman, Belleville, Ill.

[73] Assignee: Ethyl Corporation, Richmond, Va.

[21] Appl. No.: 211,273

[22] Filed: Jun. 24, 1988

[51] Int. Cl.$^4$ .............................................. C07C 37/14
[52] U.S. Cl. .................................... 568/789; 568/780; 568/794
[58] Field of Search ................................ 568/789, 794

[56] References Cited

U.S. PATENT DOCUMENTS 2,831,898  4/1958  Ecke et al. ........................... 568/789
3,355,504 11/1967  Codfield et al. ..................... 568/789
4,560,809 12/1985  Goins et al. ......................... 568/789

FOREIGN PATENT DOCUMENTS 2736059  2/1978  Fed. Rep. of Germany ...... 568/794
0252439 12/1985  Japan ................................... 568/789
1200934  9/1986  Japan ................................... 568/789

Primary Examiner—Werren B. Lone
Attorney, Agent, or Firm—Joseph D. Odenweller

[57] ABSTRACT

Phenols are selectively orthoalkylated in higher yields by the reverse addition of a phenol-aluminum phenoxide mixture to an olefin at alkylation temperature and under pressure sufficient to maintain a liquid olefin phase.

20 Claims, No Drawings

PHENOL ALKYLATION PROCESS

BACKGROUND

Phenol can be selectively alkylated in an ortho position by following the pioneering discovery of Ecke and Kolka, U.S. Pat. No. 2,831,898. According to U.S. Pat. No. '898, phenol containing an aluminum phenoxide is reacted with olefin at elevated temperature to produce an alkylation mixture containing substantial amounts of 2-alkylphenol and 2,6-dialkylphenol as well as other isomers.

Coffield et al., U.S. Pat. No.3,355,504, describe an improvement in the orthoalkylation process wherein 2,6-dialkylphenols are made in high yield under moderate conditions by starting the process with 2-alkylphenol containing an aluminum 2-alkylphenoxide catalyst and reacting this mixture with an olefin.

SUMMARY OF THE INVENTION

It has now been discovered that orthoalkylphenol yields can be increased by changing the conventional orthoalkylation process as described by Ecke et al. to a reverse feed process in which the phenol containing the aluminum phenoxide catalyst is added to the olefin alkylating agent or mixture of phenol and olefin instead of feeding the olefin to the phenol-catalyst mixture. Further benefits are achieved by conducting the process in two stages. In the first stage, the phenol-catalyst mixture is fed to the olefin or mixture of phenol and olefin at a temperature of about 85°–175° C. following which the temperature is lowered to about 25°–80° C. and the alkylation is completed at the lower temperature.

DESCRIPTION OF THE PREFERRED EMBODIMENTS

A preferred embodiment of the invention is a process for selectively orthoalkylating phenol, said process comprising:

(A) introducing an aluminum phenoxide catalyst into phenol to form a phenol-catalyst mixture, (B) placing an olefin and optionally additional phenol in a reaction vessel in an amount to provide about 1–5 moles of said olefin per total moles of phenol in said phenol-catalyst mixture and reaction vessel and maintaining said olefin under pressure sufficient to maintain a liquid olefin phase at the reaction temperature, (C) feeding said phenol-catalyst mixture to said liquid olefin at a reaction temperature of about 90°–180° C., (D) allowing the reaction to continue until a substantial amount of an orthoalkylphenol is formed and (E) recovering said orthoalkylphenol, with the further proviso that the mole ratio of total phenol to aluminum phenoxide is about 20–800.

The aluminum phenoxide catalyst can be introduced into the phenol to form the phenol-catalyst mixture in any manner. It can be separately prepared and added to the phenol. Alternatively aluminum metal can be added directly to the phenol in the proper amount and the mixture stirred and heated to about 150° C. to cause phenoxide formation. A reactive aluminum compound such as aluminum hydride, trimethyl aluminum, triethyl aluminum, diethyl aluminum hydride, diethyl aluminum chloride, triisobutyl aluminum and the like can be added to react with phenol and form an aluminum phenoxide catalyst.

The phenol is preferably dry but need not be bone-dry. Water content up to 0.05% is acceptable although it is preferred to keep water content under 0.03 weight percent. Commercial grade phenol is available for use in the process. Dry phenol allows use of less aluminum or reactive aluminum compound.

Olefins used in the process include any olefin capable of alkylating phenol such as propylene, isobutylene, 1-butene, 2-pentene, 2-ethyl-1-hexene, 1-dodecane, cyclohexene, styrene, $\alpha$-methyl styrene, cyclopentene and the like. The preferred olefins are the mono-unsaturated aliphatic hydrocarbons containing 3–12 carbon atoms. The most preferred olefin is isobutylene.

The amount of aluminum phenoxide introduced into the phenol should be an amount that will provide about 1 mole of an aluminum phenoxide for each 20–800 moles of total phenol. Total phenol is the sum of the phenol in the phenol-catalyst mixture and the optional phenol, if any, mixed with the initial olefin in the reaction vessel. When conducting the process entirely at 90°–180° C., a preferred amount of aluminum phenoxide is about one mole for each 20–100 moles of total phenol. When conducting the process in two stages at a high temperature followed by low temperature the preferred amount of aluminum phenoxide is one mole for each 100–800 moles of total phenol. The two-stage embodiment will be described later.

When referring to the amount of aluminum phenoxide herein it should be understood that this means the amount of aluminum phenoxide actually formed in the phenol and not the amount that could have formed from the quantity of aluminum or reactive aluminum compound added under anhydrous conditions. Commercial phenol contains some water. Likewise commercial olefin may contain some water or water could accidentally be present in the process equipment. The amount of aluminum or reactive aluminum compound added to the phenol to form the catalyst should be adjusted to compensate for any water in the phenol or olefin or any other reactive hydrogen contaminant in the system that could destroy aluminum phenoxide.

The process can be conducted by charging the olefin to a pressure reaction vessel and heating the olefin to reaction temperature. Optionally additional phenol can be placed in the reaction vessel with the olefin. The amount of olefin should be at least one mole per total moles of phenol in the phenolcatalyst mixture and reaction vessel. A useful range in which to experiment in order to optimize results is about 1–5 moles of olefin per mole of total phenol depending on the degree of alkylation desired. When the desired product is a 2,6-dialkylphenol the preferred total amount of olefin is in the range of about 1.5–2.5 moles per mole of total phenol and most preferably about 2.05–2.3 moles per mole of total phenol.

It is not essential that any phenol be mixed with the initial olefin charge. All of the phenol can be in the phenolcatalyst mixture. This is the reason the phenol initially added to the reaction vessel is referred to as "and optionally additional phenol" because it need not be added as long as the phenol in the phenol-catalyst mixture is sufficient to satisfy the total phenol to aluminum phenoxide ratio.

In a preferred embodiment a portion of the total phenol is added to the pressure reaction vessel together with the olefin. A useful amount of phenol to mix with the initial olefin is about 10-75 weight percent of the total phenol used in the process. A more preferred amount of the optional phenol is about 25-70 weight percent of the total phenol and still more preferably about 40-60 weight percent of the total phenol.

All of the olefin may be charged to the reactor at the start or a portion may be charged to form a starter liquid phase and the rest charged during the reaction. Preferably at least half of the total olefin is charged at the start of the reaction. More preferably at least 75 percent of the required olefin is initially charged to the reactor. Still more preferably at least 90 percent of the olefin is initially charged and most preferably all of the olefin to be used is placed in the reactor at the start of the process.

The olefin and optional phenol, if any, are then heated to reacion temperature. In the one-stage process this is in the range of about 90°-180° C., more preferably about 90°-110° C. Vapor pressure of the lower olefins, e.g., propylene, isobutylene, isopentene, etc., will be quite high so an adequate pressure resistant autoclave should be used. Of course, certain olefins have a relatively low critical temperature and will not form a distinct liquid-gas system above this temperature. For example, propylene has a critical temperature of only 91.9° C. and exhibits a critical pressure of 45.4 bars at this temperature. Isobutylene has a critical temperature of 144.7° C. Hexene-1 has a critical temperature of 231° C., cyclopentene 232.9° C. and cyclohexene 287.3° C. It is most preferred that the process be conducted below the critical temperature of the olefin to provide a liquid olefin phase. Hence with propylene the preferred temperature is below 91.9° C., e.g. 80°-90° C., and is an exception to the above stated preferred and more preferred temperature range.

The phenol-catalyst mixture is fed to the olefin and optional phenol at reaction temperature. In an equivalent mode of operation, phenol and a catalyst concentrate are co-fed to the olefin. The catalyst concentrate contains an aluminum phenoxide and is fed in an amount that when combined with the phenol feed and optional phenol, if any, mixed with the olefin will provide the desired aluminum phenoxide to phenol mole ratio.

The phenol-catalyst mixture is preferably fed to the olefin at the highest rate at which the reaction temperature can still be controlled. After the phenol-catalyst mixture feed is complete, reaction is continued at reaction temperature until the amount of desired orthoalkylphenol reaches the desired concentration. This is usually the maximum concentration of the desired product but may be somewhat less than maximum if the economics of the process become better at a lower yield.

The following example shows how the conventional phenol alkylation process is conducted and compares this with the way the new reverse-feed process is conducted. All parts are by weight.

EXAMPLE 1

Conventional OrthoAlkylation

In an autoclave was placed 2447 parts (26 moles) of phenol. The autoclave was flushed with nitrogen and 114.1 parts (1 mole) of triethylaluminum was added. The mixture was heated to 150° C. to form aluminum phenoxide catalyst. The reaction mixture was cooled and the evolved ethane was vented. Then, 2917 parts (52 moles) of isobutylene was fed into the autoclave at 100° C. and 200-300 psig over a 1-hour period. The mixture was stirred at 100° C. for 3-4 hours and then cooled and washed with acidic water to remove aluminum. The reaction composition (analysis by gas chromatography, GC) is shown in Table I.

EXAMPLE 2

Reverse Feed OrthoAlkylation

A phenol-catalyst mixture was prepared by adding 114.1 parts (1 mole) of triethylaluminum to 2447 parts (26 moles) of phenol and stirring the mixture at 150° C.

To a high pressure autoclave was charged 2917 parts (52 moles) of isobutylene. The autoclave was sealed and heated to 100° C., 260 psig. While stirring the phenol-catalyst mixture was pumped into the autoclave over a 1-hour period at 100° C. Stirring was continued at 100° C. for 4 hours and then the mixture was cooled, vented and washed with acidic water. The composition is shown in Table I.

TABLE I

| Component | Example 1 | Example 2 |
|---|---|---|
| phenol | 3.1 | 2.1 |
| 2-tert-butylphenol | 8.5 | 17.3 |
| 2-tert-butylphenyl ether | 0.8 | 0.7 |
| 2,6-di-tert-butylphenol | 74.3 | 71.7 |
| 2,4-di-tert-butylphenol | 1.7 | 1.7 |
| 2-tert-octylphenol | 0.7 | 0.4 |
| 2,4,6-tri-tert-butylphenol | 10.7 | 5.7 |
| 4-tert-butylphenol | 0.1 | 0.2 |

Example 1 contained somewhat more 2,6-di-tert-butylphenol than Example 2. However, Example 2 contained twice as much 2-tert-butylphenol (17.3 percent vs. 8.5 percent). Since 2-tert-butylphenol can be alkylated further in a subsequent cycle, it can be included as an orthoalkylated product. Hence the effective orthoalkyl phenol is higher in Example 2. Also Example 2 contains less para-alkylated phenols. These are undesirable.

In another mode of operation the process is conducted in two stages at different temperatures. This embodiment is a two-stage process for selectively orthoalkylating phenol, said process comprising:

(A) introducing an aluminum phenoxide catalyst into phenol to form a phenol-catalyst mixture, (B) placing an olefin and optionally additional phenol in a reaction vessel in an amount to provide about 1-5 moles of said olefin per mole of total phenol in said phenol-catalyst mixture and said reaction vessel and maintaining said olefin under pressure sufficient to maintain a liquid olefin phase at the reaction temperature, (C) in a first stage, feeding said phenol-catalyst mixture to said liquid olefin and optional phenol in said reaction vessel at a reaction temperature of about 85°-175° C.

(D) allowing the reaction of phenol and olefin to continue at 85°-175° C. until the amount of phenol decreases to about 3 weight percent or less of the reaction mixture, (E) lowering the reaction temperature to 25°-80° C., (F) in a second stage, continuing the reaction at 25°-80° C. until the amount of orthoalkylphenol reaches the desired level and (G) recovering the desired orthoalkylphenol, with the further proviso that the mole ratio of total phenol used in the process to aluminum phenoxide is 100-800:1.

The aluminum phenoxide-phenol mixture is prepared in the same manner as in the one-stage process. Although the two-stage process is operable over the range of 1 mole aluminum phenoxide for each 20-800 moles of total phenol, or even a broader range can be used, it is more preferred in this embodiment to reduce the amount of aluminum phenoxide to 1.0 mole per each 100-800 moles of total phenol. An even more preferred amount of catalyst is 1.0 mole for each 150-500 moles of total phenol and most preferably for each 180-300 moles of total phenol. If the reactants are wet, additional aluminum or reactive aluminum compound may be required to compensate for catalyst hydrolyzed by water.

The olefins used in this two-stage embodiment are the same as in the one-stage process with isobutylene being the most preferred olefin.

The amount of olefin used is the same as in the previous one-stage procedure, i.e. about 1-5 moles per mole of total phenol. For di-orthoalkylation, the preferred amount of olefin is about 1.5-2.5 moles and most preferably about 2.05-2.3 moles per mole of phenol.

The process is conducted in two stages. In the first stage the phenol-catalyst mixture is fed to the olefin in a liquid phase at about 85°-175° C. preferably 100°-150° C. and more preferably 110°-125° C. As before, it is not essential that all of the olefin be initially charged to the autoclave but it is necessary that a substantial portion, e.g. at least 50%, be initially charged so that the initial phenol-catalyst feed is met in the reaction vessel with a large olefin excess. More preferably at least 75 percent of the required olefin is initially charged and still more preferably at least 90 percent of the olefin is initially charged.

If the entire amount of olefin used in the process is not initially placed in the reaction vessel, the deficiency can be made up by feeding additional olefin during the first stage reaction, after the first stage reaction or both during and after the first stage reaction in amounts such that the total olefin used in the process is 1-5 moles per mole of total phenol used in the process, more preferably 1.5-2.5 moles and most preferably 2.05-2.3 moles per mole of total phenol used in the process.

In a highly preferred embodiment, 1.7-2.0 moles of isobutylene per mole of total phenol is initially charged to the reaction vessel and additional isobutylene is charged between the first and second reaction stage such that the total amount of isobutylene used is 2.05-2.3 moles per mole of total phenol used.

The first stage reaction temperature is about 85°-175° C., more preferably about 100°-150° C. still more preferably 110°-125° C. and most preferably about 115° C. The phenol-catalyst mixture is preferably fed at as fast a rate as can be maintained and still permit temperature control.

After the phenol-catalyst mixture feed is complete the reaction is stirred at first stage reaction temperature until the phenol content of the reaction mixture drops to about 3 weight percent or less, more preferably about 2 weight percent or less and most preferably 1 weight percent or less.

The reaction temperature is then lowered into the range of about 25°-80° C., more preferably 50°-70° C. and the reaction continued with stirring until the concentration of the desired orthoalkylphenol is optimized. The optimum concentration will vary depending upon the olefin selected and the economics involved taking into account credit for some by-products. When the desired product is 2,6-di-tertbutylphenol the optimum concentration in the reaction product is in excess of 75 weight percent and more preferably over 80 weight percent.

The following example shows the reverse feed process using the two-stage embodiment.

EXAMPLE 3

A phenol-catalyst mixture was made by adding 114 parts (1 mole) of triethylaluminum to 9575 parts (101.86 moles) of phenol and stirring while heating to about 150° C.

To a separate autoclave charged 8792 parts (93.5 moles) of phenol and 17154 parts (300.9 moles) of isobutylene. The reactor was stirred and heated to 115° C. The phenol-catalyst mixture was then fed to the phenol-isobutylene mixture at a constant rate over 45 minutes at 115° C. Cooling was required. Stirring was continued at 115° C. while 6178 parts (108.4 moles) of additional isobutylene was added over a 1-hour period. At 2 hours from completion of phenol-catalyst feed the pressure had dropped to 120 psig from maximum of 300 psig.

The autoclave was then cooled to 70° C. for the second stage reaction. While cooling from 115° to 70° C. an additional 1705 parts (29.9 moles) of isobutylene was pumped into the autoclave. Time for cool-down was 20 minutes. Stirring was then continued at 70° C. for 2 hours 10 minutes. The final reaction mixture was washed with acidic water and analyzed by GC. The results are shown in Table II.

Following Example 4 shows the results of a similar 2-stage process but without the reverse-feed modification of Example 3.

EXAMPLE 4

In a reaction vessel was placed 8100 parts of phenol and 27 parts of aluminum metal. The vessel was sealed and heated to 150° C. to form aluminum triphenoxide. This catalyst concentrate was then mixed with 11,124 parts of additional phenol. This gives a phenol-/aluminum mole ratio of about 203. The phenolcatalyst mixture was cooled to 90° C. and 23,490 parts of isobutylene was pumped in over a 50-minute period. The reaction temperature rose to 110° during the first 10 minutes of isobutylene feed. Stirring was continued at 110°-115° C. for 165 minutes. Reactor pressure dropped to 120 psig from a maximum of 260 psig.

Cooling was then applied to lower the temperature to 70° C. over a 45-minute period. An additional 1728 parts of isobutylene was then pumped in and the reaction mixture stirred for an additional 90 minutes at 70° C. The reaction mixture was analyzed by GC and had the composition shown in Table II.

TABLE II

| Component | Example 3 | Example 4 |
|---|---|---|
| 2,6-di-tert-butylphenol | 87.5 | 82.7 |
| 2-tert-butylphenol | 2.2 | 2.0 |
| 2,4-di-tert-butylphenol | 0.3 | 0.4 |
| 2,4,6-tri-tert-butylphenol | 8.1 | 13.2 |
| 4-tert-butylphenol | — | — |
| 2-tert-octylphenol | 0.4 | 0.6 |
| 2-tert-butylphenol tert-butyl ether | 1.5 | 1.0 |
| phenol | — | 0.1 |

These results show that the reverse feed is an improvement over the direct feed 2-stage process which is itself a new process described in application Ser. No. 211,295 filed herewith by S. L. Wiker, C. W. Matthews and J. F. King entitled "Phenol Alkylation Process" and designated Case No. 5774.

We claim:

1. A process for selectively orthoalkylating phenol, said process comprising:
    (A) introducing an aluminum phenoxide catalyst into phenol to form a phenol-catalyst mixture,
    (B) placing an olefin in a reaction vessel in an amount to provide about 1–5 moles of said olefin per mole of total phenol in said phenol catalyst mixture and reaction vessel and maintaining said olefin under pressure sufficient to maintain a liquid olefin phase at the reaction temperature,
    (C) feeding said phenol-catalyst mixture to said liquid olefin at a reaction temperature of about 90°–180° C.,
    (D) allowing the reaction of phenol and olefin to continue until a substantial amount of an orthoalkylphenol is formed and
    (E) recovering said orthoalkylphenol, with the further proviso that the mole ratio of total phenol used in the process to aluminum phenoxide is about 20–800:1.

2. A process of claim 1 wherein said olefin is isobutylene.

3. A process of claim 2 wherein the amount of said isobutylene is about 2.05–2.3 moles per mole of said total phenol.

4. A process of claim 3 wherein said reaction temperature is about 90°–110° C.

5. A two-stage process for selectively orthoalkylating phenol, said process comprising:
    (A) introducing an aluminum phenoxide catalyst into phenol to form a phenol-catalyst mixture,
    (B) placing an olefin in a reaction vessel in an amount to provide about 1–5 moles of said olefin per mole of total phenol in said phenol-catalyst mixture and reaction vessel and maintaining said olefin under pressure sufficient to maintain a liquid olefin phase at the reaction temperature,
    (C) in a first stage, feeding said phenol-catalyst mixture to said liquid olefin and phenol in said reaction vessel at a reaction temperature of about 85°–175° C.,
    (D) allowing the reaction of phenol and olefin to continue at 85°–175° C. until the amount of phenol decreases to about 3 weight percent or less of the reaction mixture,
    (E) lowering the reaction temperature to 25°–80° C.,
    (F) in a second stage, continuing the reaction at 25°–80° C. to complete the alkylation and
    (G) recovering the desired orthoalkylphenol product with the further proviso that the mole ratio of total phenol used in the process to aluminum phenoxide is 100–800:1.

6. A process of claim 5 wherein said olefin is isobutylene.

7. A process of claim 6 wherein said reaction temperature in step (C) is about 110°–125° C.

8. A process of claim 7 wherein the total amount of isobutylene used in the process is about 1.5–2.5 moles per total mole of phenol in said phenol-catalyst mixture and said reaction vessel 9. A process of claim 8 wherein the amount of aluminum phenoxide in step (A) is sufficient to provide 1 mole of said aluminum phenoxide per each 150–500 moles of said total phenol in said phenol-catalyst mixture and said reaction vessel.

10. A process of claim 9 wherein step (F) is conducted at about 50°–70° C.

11. A process of claim 8 wherein the amount of isobutylene placed in said reaction vessel in step (B) is about 2.05–2.3 moles per mole of phenol in said phenol-catalyst mixture and said reaction vessel.

12. A process of claim 8 wherein the amount of isobutylene placed in the reaction vessel in step (B) is 1.7–2.0 moles per mole of said total phenol and an additional quantity of isobutylene is added to said reaction vessel between the first and second stages such that the total isobutylene added to the reaction vessel is about 2.05–2.3 moles per mole of said total phenol.

13. A process of claim 1 further characterized by including additional phenol in the olefin placed in the reaction vessel in step (B), the amount of said additional phenol being an amount which provides about 10–75 weight percent of the total phenol used in the process.

14. A process of claim 13 wherein the amount of said additional phenol is an amount which provides about 40–60 weight percent of the total phenol used in the process.

15. A process of claim 13 wherein said olefin is isobutylene.

16. A process of claim 15 wherein the total amount of said isobutylene is about 2.05–2.3 moles per mole of said total phenol.

17. A process of claim 5 further characterized by including additional phenol in the olefin placed in the reaction vessel in step (B), the amount of said additional phenol being an amount which provides about 10–75 weight percent of the total phenol used in the process.

18. A process of claim 17 wherein the amount of said additional phenol is an amount which provides about 40–60 weight percent of the total phenol used in the process.

19. A process of claim 17 wherein said olefin is isobutylene.

20. A process of claim 19 wherein the total amount of said isobutylene is about 2.05–2.3 mole of said total phenol.

* * * * *

UNITED STATES PATENT AND TRADEMARK OFFICE
CERTIFICATE OF CORRECTION

PATENT NO. : 4,870,216

DATED : SEPTEMBER 26, 1989

INVENTOR(S) : JEFFREY F. KING ET AL.

It is certified that error appears in the above-identified patent and that said Letters Patent is hereby corrected as shown below:

Column 8, line 55 reads "2.05-2.3 mole" and should read -- 2.05-2.3 moles per mole -- .

Signed and Sealed this

Twenty-fifth Day of September, 1990

Attest:

HARRY F. MANBECK, JR.

*Attesting Officer*     *Commissioner of Patents and Trademarks*